United States Patent [19]

Vasconcellos et al.

[11] Patent Number: 4,923,438

[45] Date of Patent: May 8, 1990

[54] BLOOD RECOVERY SYSTEM AND METHOD

[75] Inventors: Alfred V. Vasconcellos, Edison, N.J.; Preston J. Keeler, III, Setauket, N.Y.

[73] Assignee: Pfizer Hospital Products Group, Inc., New York, N.Y.

[21] Appl. No.: 220,193

[22] Filed: Jul. 18, 1988

[51] Int. Cl.[5] .............................................. A61M 1/03
[52] U.S. Cl. ........................................ 604/4; 604/319
[58] Field of Search ........................................ 604/4–6, 604/317, 319–321, 323, 350

[56] References Cited

U.S. PATENT DOCUMENTS

| | | | |
|---|---|---|---|
| 2,745,111 | 5/1956 | Podmorski | 604/350 X |
| 2,759,476 | 8/1956 | Henderson | 604/319 X |
| 3,585,995 | 6/1971 | Perkins et al. | 604/4 X |
| 3,896,733 | 7/1975 | Rosenberg | 604/9 X |
| 4,006,745 | 2/1977 | Sorenson et al. | 128/214 R |
| 4,033,345 | 7/1977 | Sorensen et al. | 128/214 R |
| 4,047,526 | 9/1977 | Reynolds et al. | 128/214 R |

Primary Examiner—Dalton L. Truluck
Attorney, Agent, or Firm—Peter C. Richardson; Lawrence C. Akers; John L. LaPierre

[57] ABSTRACT

An intraoperative blood recovery system and method for salvaging operative blood while simultaneously delivering previously collected blood to a reinfusion system. A blood collection and transfer reservoir, having multiple compartments which can be separated by vacuum or pressure barriers, is designed to maintain a continuous suction for blood inflow while blood previously collected can be simultaneously transported through the reservoir to achieve an uninterrupted flow of blood into and delivery of blood out of the reservoir.

43 Claims, 8 Drawing Sheets

BLOOD RECOVERY SYSTEM AND METHOD

BACKGROUND OF THE INVENTION

The present invention generally relates to blood collection systems and methods of blood collection and, more particularly, it relates to autologous blood recovery systems, methods of blood recovery and blood transfer, and blood collection reservoirs, wherein blood recovery receptacles connected to a suction source can simultaneously collect and release blood.

There have been introduced into the marketplace a number of direct whole blood cardiotomy reservoirs and methods for using reservoirs during the recovery and collection of blood for subsequent reinfusion into a patient. Typically, a system might utilize a negative pressure source for blood delivery and collection in a reservoir and use the force of gravity for return of the collected blood to the patient. Alternatively, instead of using gravity, a roller pump or an intravenous pump might be used for reinfusion of blood collected to increase the rate of blood return to the patient. In each system, the blood collection reservoir cannot be used to simultaneously collect blood using negative pressure and reinfuse the blood using positive pressure, gravity or pressure above atmospheric.

Other autotransfusion systems in the marketplace incorporate disposable flexible liners in either blood collection or blood transfer reservoirs. In one instance, during blood collection, a negative pressure source is used to convey blood to the collection reservoir and thereafter the collected blood is transferred to a second liner reservoir for gravity feed return to the patient. If desired, the second liner reservoir can be subjected to external pressurization, internal pressurization cannot be utilized because of liner flexibility, to enhance the rate of blood reinfusion. As before, this type of system is not capable of simultaneously drawing and reinfusing blood. An additional disadvantage of this type system is that suction in the surgical field can be interrupted during liner changes.

Another marketplace liner system employs a liner reservoir in a single used hard plastic housing. The system utilizes negative pressure to convey blood from the operative field into the liner. When the liner is full, another unit is used. The first liner reservoir is then removed for blood processing or for reinfusion directly into the patient. Reinfusion may be achieved utilizing gravity or the rigid housing may be pressurized to accelerate reinfusion. As with the foregoing systems, this system is not capable of simultaneous blood collection and blood reinfusion. Also, the liner reservoir is a single use disposable item.

The liner reservoir systems have not been entirely satisfactory in the blood collection field. The systems have a long history of liner leaks and failure to adequately serve the surgical community. Additionally, the systems are labor intensive and difficult to handle when not routinely used.

The primary objective of the present invention is to advance the art field of surgical autologous blood recovery by providing a unique blood collection reservoir for use in intraoperative blood recovery systems. A characteristic feature of the collection reservoir, which is not found in the aforementioned systems devices, is its capability of maintaining a continuous predetermined suction while emptying the contents just previously collected in the reservoir. The simultaneous fill and draw property of the present reservoir cannot be found in existing blood collection reservoirs. Also, the reservoir eliminates the attendant disadvantages previously noted with respect to known systems reservoirs (leaking, suction interruption, pressurization, single use) and presents a simple, uncomplicated, multi compartment device which is easy to manufacture and use. Accordingly, we have invented an improved blood collection reservoir and system uniquely capable of simultaneously achieving an uninterrupted flow of blood into the reservoir for collection while releasing collected blood from the reservoir for processing or reinfusions.

SUMMARY OF THE INVENTION

The invention pertains to a novel fluid collection reservoir, particularly suitable for collecting blood, wherein the reservoir comprises an inlet and an outlet, a plurality of fluid collecting compartments, means for establishing a negative pressure in two or more of the compartments, and means for selectively isolating each of the compartments for collecting and transferring fluid through the reservoir. Preferably, the reservoir has three compartments. Fluid may flow out of the reservoir under gravity conditions or a pressure source may be provided to assist in delivery of fluid out of the reservoir. The reservoir might additionally include a first filter for gross particulate removal and foam reduction and a second filter for bacteria removal. Also, the reservoir might include a means for equalizing pressure between contiguous compartments.

In one embodiment, the reservoir is a blood collection reservoir comprising a housing defining a collection chamber having a plurality of compartments; an inlet for introducing blood into the collection chamber; means for providing fluid flow communication between a first of the compartments and a second of the compartments; means for creating a first fluid seal between the second compartment and a third of the compartments; means for establishing a negative pressure in the first and the second compartments; means for creating a second fluid seal between the first and the second compartments while maintaining the first fluid seal; means for releasing the first fluid seal and providing fluid flow communication between the second and the third compartments; and an outlet for conveying blood out of the collection chamber. The reservoir might further include means for reestablishing the first fluid seal, and means for releasing the second fluid seal and reestablishing fluid flow communication between the first and the second compartments while maintaining the reestablished first fluid seal. Also provided is a means for equalizing pressure between the second and the third compartments before releasing the first fluid seal. Further contemplated to be within the scope of the invention is an autologous blood recovery system employing the blood collection reservoir.

The present invention further contemplates a blood collection method comprising the steps of
(a) establishing a connection between a reservoir and an inlet of a housing including a collection chamber having a plurality of compartments, said inlet being in fluid flow communication with said collection chamber;
(b) providing fluid flow communication between a first of said compartments and a second of said compartments;

(c) creating a first fluid seal between said second compartment and a third of said compartments;
(d) establishing a negative pressure in said first and said second compartments, with said negative pressure being sufficient for conveying and maintaining a flow of blood from said reservoir into said collection chamber;
(e) introducing said blood into said first compartment for passage therethrough and collection in said second compartment;
(f) creating a second fluid seal between said first and said second compartments while maintaining said first fluid seal and collecting blood in said first compartment;
(g) releasing said first fluid seal providing fluid flow communication between said second and said third compartments, passing into said third compartment blood collected in said second compartment; and
(h) establishing a connection between an outlet in said collection chamber and a patient for conveying and infusing the blood into said patient.

Additionally included could be the steps of
(i) reestablishing said first fluid seal; and
(j) releasing said second fluid seal and reestablishing fluid flow communication between said first and said second compartments while maintaining said reestablished first fluid seal, passing into said second compartment blood collected in said first compartment.
followed by the steps of
(k) maintaining said negative pressure; and
(l) repeating steps e through k, thereby maintaining an uninterrupted flow of blood into and delivery of blood out of said collection chamber.

An alternative method would include the added step of establishing a positive pressure in said third compartment. Further contemplated to be within the scope of the invention is an autologous blood collection method.

The various features of novelty which characterize the invention are pointed out with particularity in the claims annexed to and forming a part of this disclosure. For a better understanding of the invention, its operating advantages and specific results obtained by its use, reference should be made to the corresponding drawings and descriptive matter in which there are illustrated and described typical embodiments of the invention.

DETAILED DESCRIPTION OF THE PREFERRED EMBODIMENTS

Figure 1:
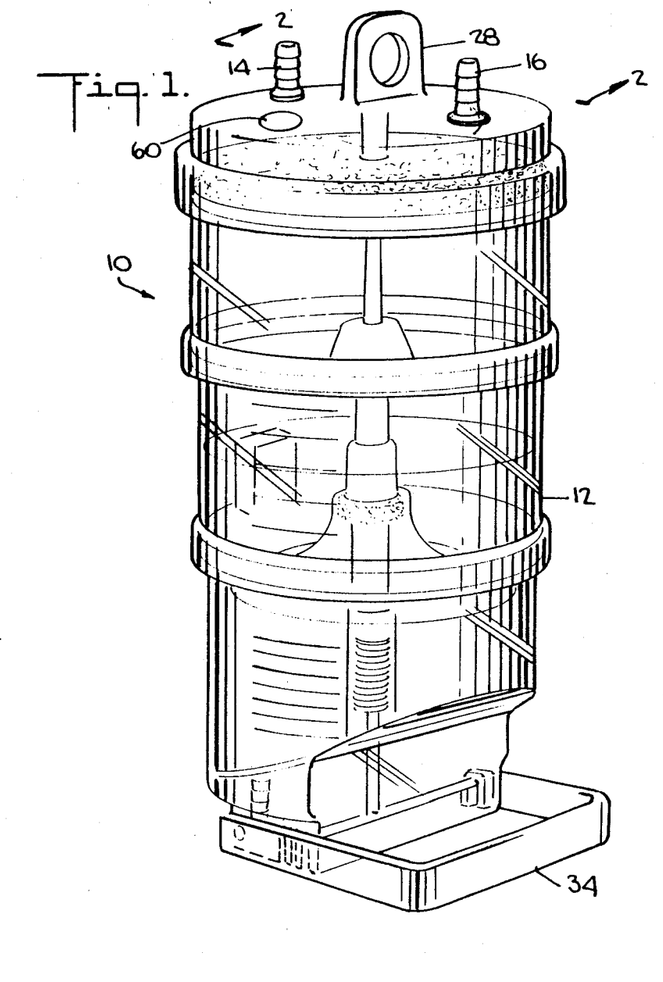
FIG. 1 is a perspective view of a fluid collection reservoir, particularly suitable for collecting blood, in accordance with the principles of the present invention, illustrating a general overall view of the reservoir.
Figure 2:
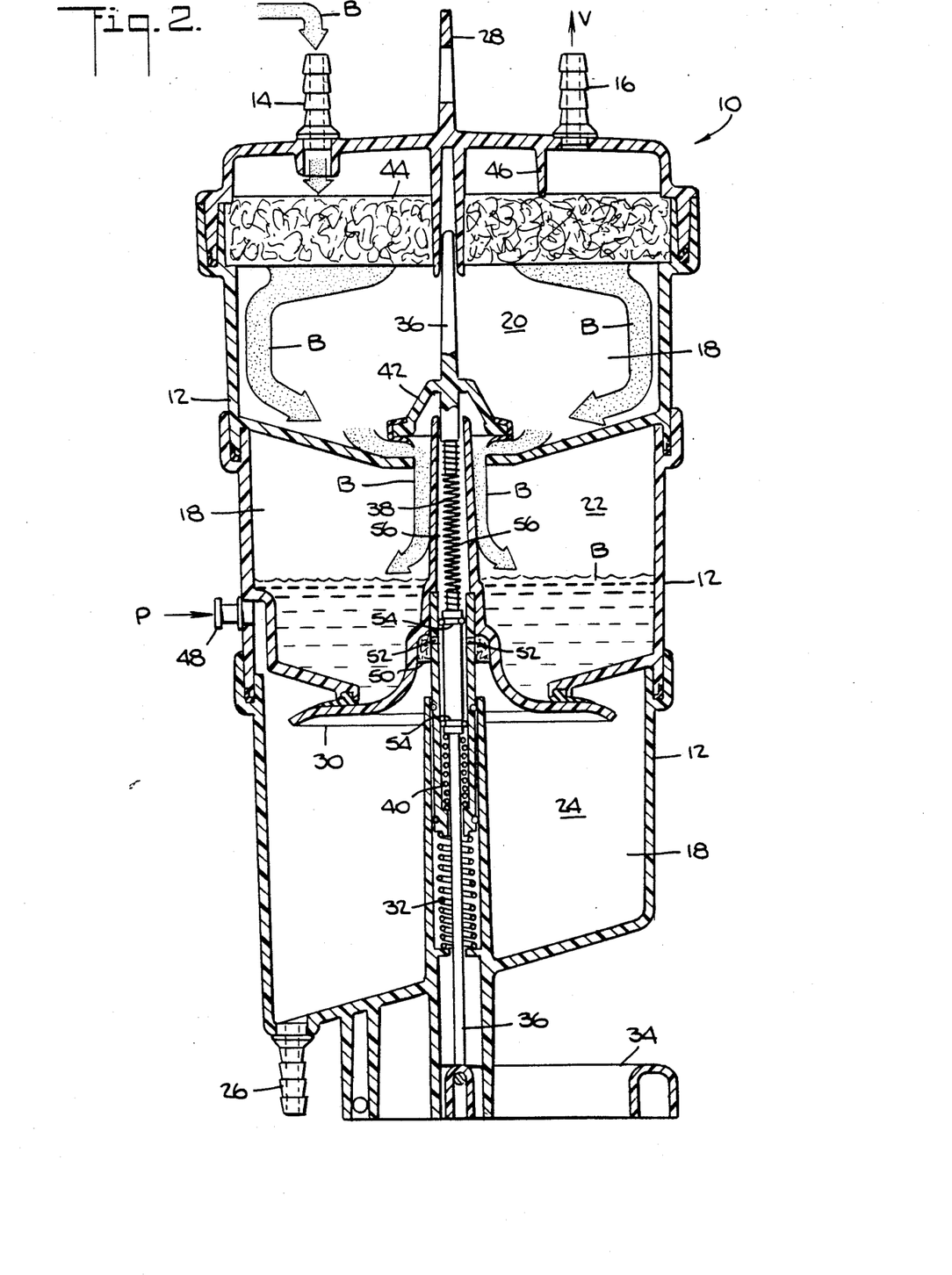
FIG. 2 is an enlarged cross-sectional view taken along line 2—2 of the reservoir depicted in FIG. 1 and showing the reservoir in a first fluid collecting operation.

The description herein presented refers to the accompanying drawings in which like reference numerals refer to like parts throughout the several views. First turning to FIG. 1, there is illustrated a perspective view of blood collection reservoir 10 of the present invention depicting a general view of the reservoir. It should be understood that, while a blood collection reservoir will be described, the reservoir would be suitable for collection of other fluids. Reservoir 10 includes rigid housing portion 12, blood inlet port 14, vacuum port 16, collection chamber 18 having compartments 20, 22 and 24, blood outlet port 26 and hanger 28. Turning next to FIG. 2, which shows the reservoir schematically in a first blood collection step, with blood B shown entering inlet 14 upon the imposition of a vacuum V through vacuum port 16. Inlet 14 is connected to a blood source and vacuum port 16 is connected to a suitable source of suction. Compartments 20 and 22 are in fluid flow communication, both compartments being under vacuum, through a central opening through which the blood flows into compartment 22 for collection. Compartments 22 and 24 are sealed off from one another by means of valve 30 which forms a fluid tight seal between the two compartments. Valve 30 is held closed by spring 32, which is under compression, causing the seating of the valve and sealing of a central opening between compartment 22 and 24. Also shown in FIG. 2 is lever 34 engaging elongated member or rod 36 (the upper portion in this view being coupled to the lower portion by spring 38), spring 40 and valve 42 being supported by member 36. Additionally provided are filter 44, used for gross particulate removal and foam reduction, and baffle 46 which serves to divert blood away from vacuum port 16 to keep blood from exiting through the vacuum port. There is furthermore provided a port 48 which can serve to selectively pressurize compartment 24 as shown by P. Pressurization P can be achieved by using a sphygmomanometer bulb, a pressure gauge, and tubing (all of which are not shown) communicating with port 48. Pressure is preferably maintained from about atmospheric up to about 200 millimeters of mercury. Pressurizing air or gas entering compartment 24 through port 48 may be filtered using a bacterial filter (not shown) having a pore size less than one micron but preferably a pore size equal to or less than 0.45 microns. Alternatively, port 48 can be used to vent compartment 24 to atmosphere or ambient and, in this situation, a bacterial filter could also be used to prevent blood contamination. Lastly shown in FIG. 2, are filter 50, vents 52, seal rings 54 and passageway or channel 56. In this view, seal rings 54 close passageway 56 from vents 52 so that this path of communication between compartments 22 and 24, in addition to the compartmental sealing by valve 30, remains closed. However, the design is such that pressures between compartments 22 and 24 may be equalized through the displacement of seal rings 54 to open communication between vents 52 and channel 56 before valve 30 is unseated to open the larger central opening between the compartments. This equalization of pressure between compartments 22 and 24 is particularly important when compartment 24 is pressurized above atmospheric.

Figure 3:
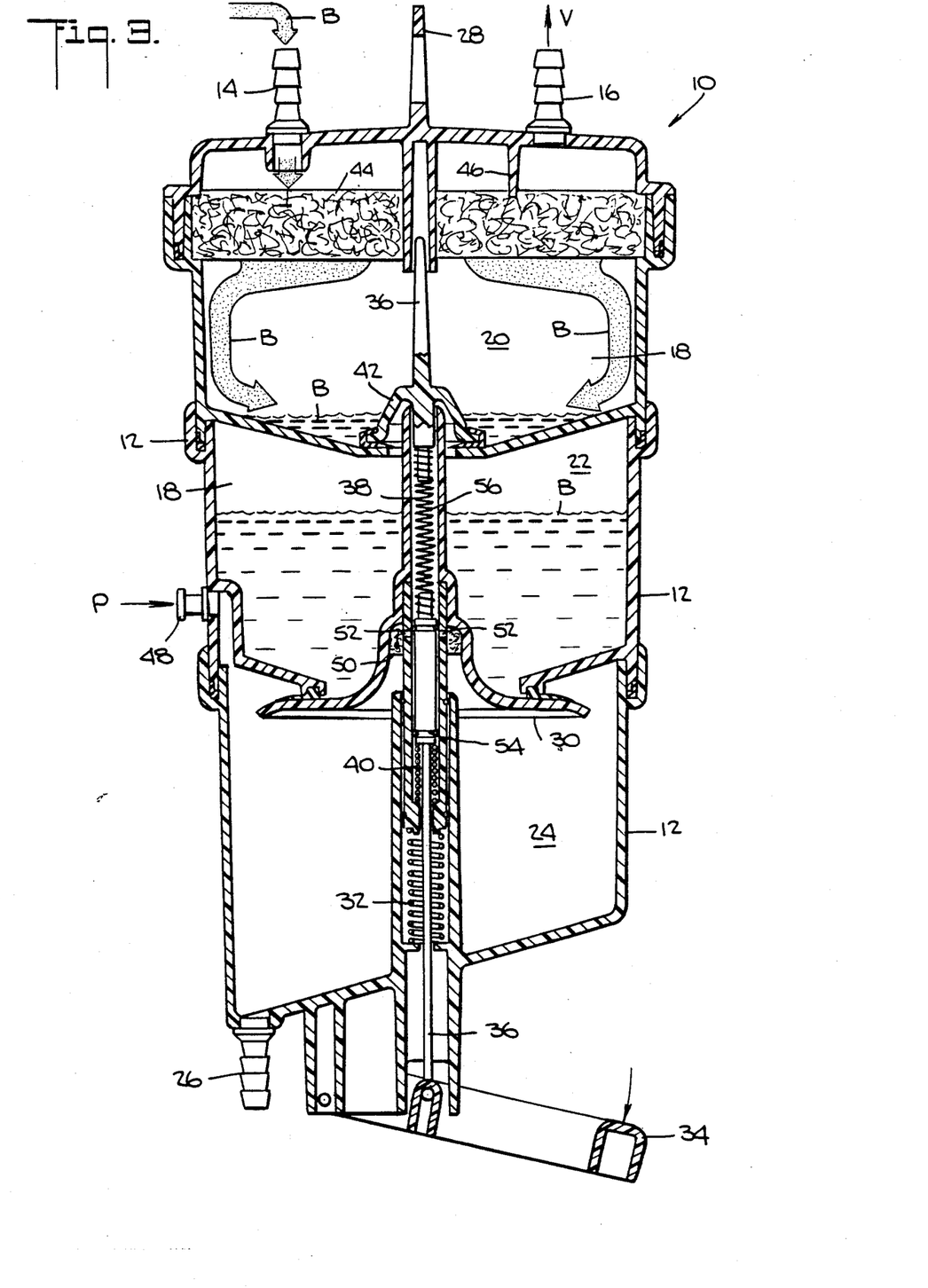
FIG. 3 is a view like that of FIG. 2 but showing an isolation and holding of previously collected fluid while additional fluid is being collected.
Figure 4:
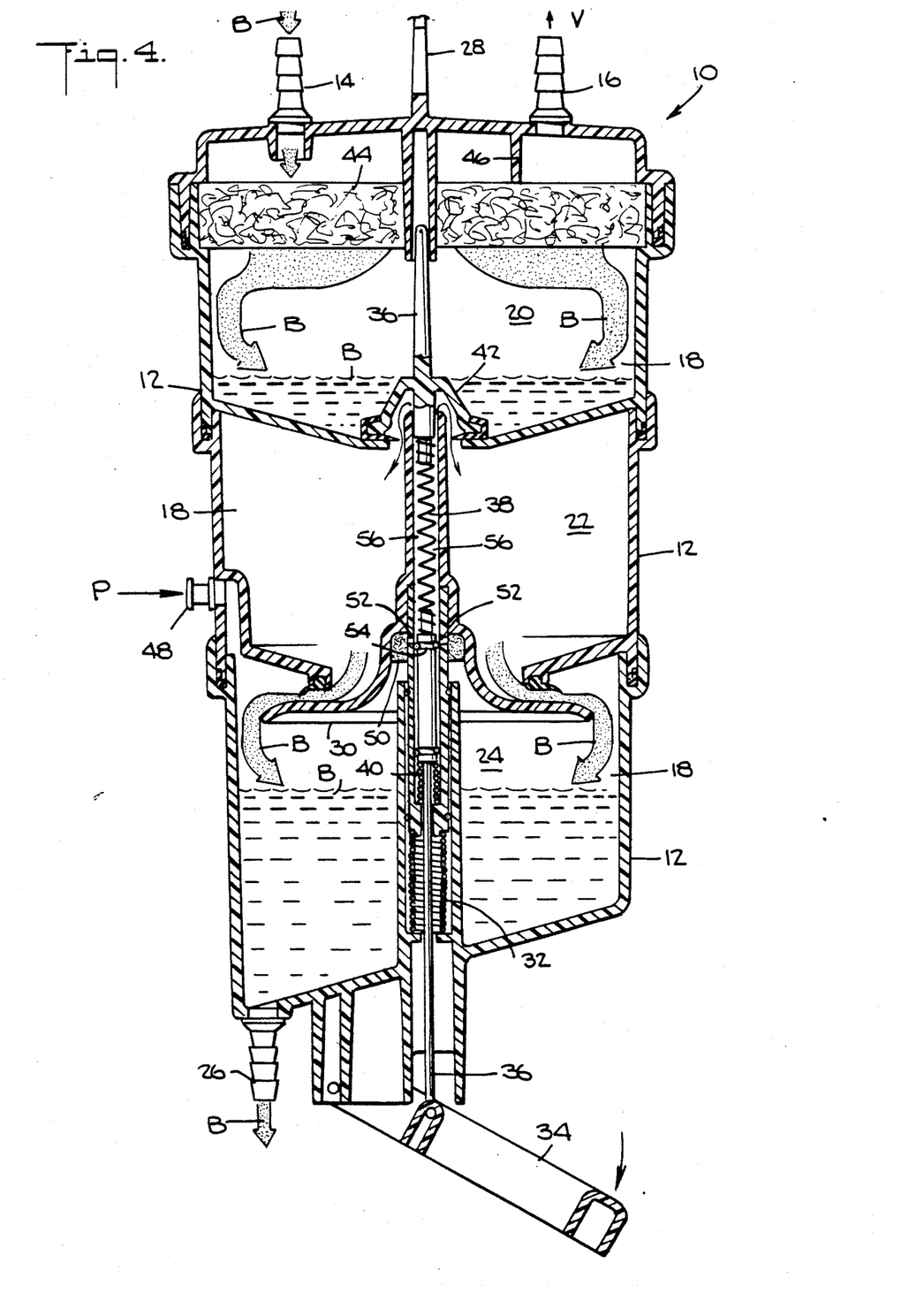
FIG. 4 is a view like that depicted in FIGS. 2 and 3 but showing the reservoir transferring fluid previously isolated and delivering fluid out of the reservoir while simultaneously collecting additional fluid.

Turning now to FIG. 3, there is shown lever 34 being moved downwardly, causing the downward displacement of member 36, and the downward movement of valve 42 which seats to seal compartments 20 and 22 from one another. Valve 30 remains closed and blood is continuously being collected in compartment 20. FIG. 4 depicts another step in the blood collection process wherein upon further downward movement of lever 34, member 36 is further displaced downwardly, spring 32 is further compressed and valve 30 is forced downwardly for unseating. It should here be noted that the pressure equalization between compartments 22 and 24 through open vents 52 and passageway 56 (see arrows) occurred after upper seal ring 54 passed vents 52 and before unseating of valve 30, with spring 38 being placed in tension and spring 40 being compressed. In this view, valve 30 is unseated, releasing the previously established seal between compartments 22 and 24, and the blood previously collected and held in compartment 22 is allowed to flow into compartment 24. Meanwhile, valve 42 remains seated and blood continues to be collected in compartment 20. Also in this view, blood is shown exiting blood outlet port 26 while blood is simultaneously being collected. Pressurization of compartment 24 is accomplished to assist in the delivery of blood out of the reservoir. Alternatively, gravity delivery could have been employed.

Figure 5:
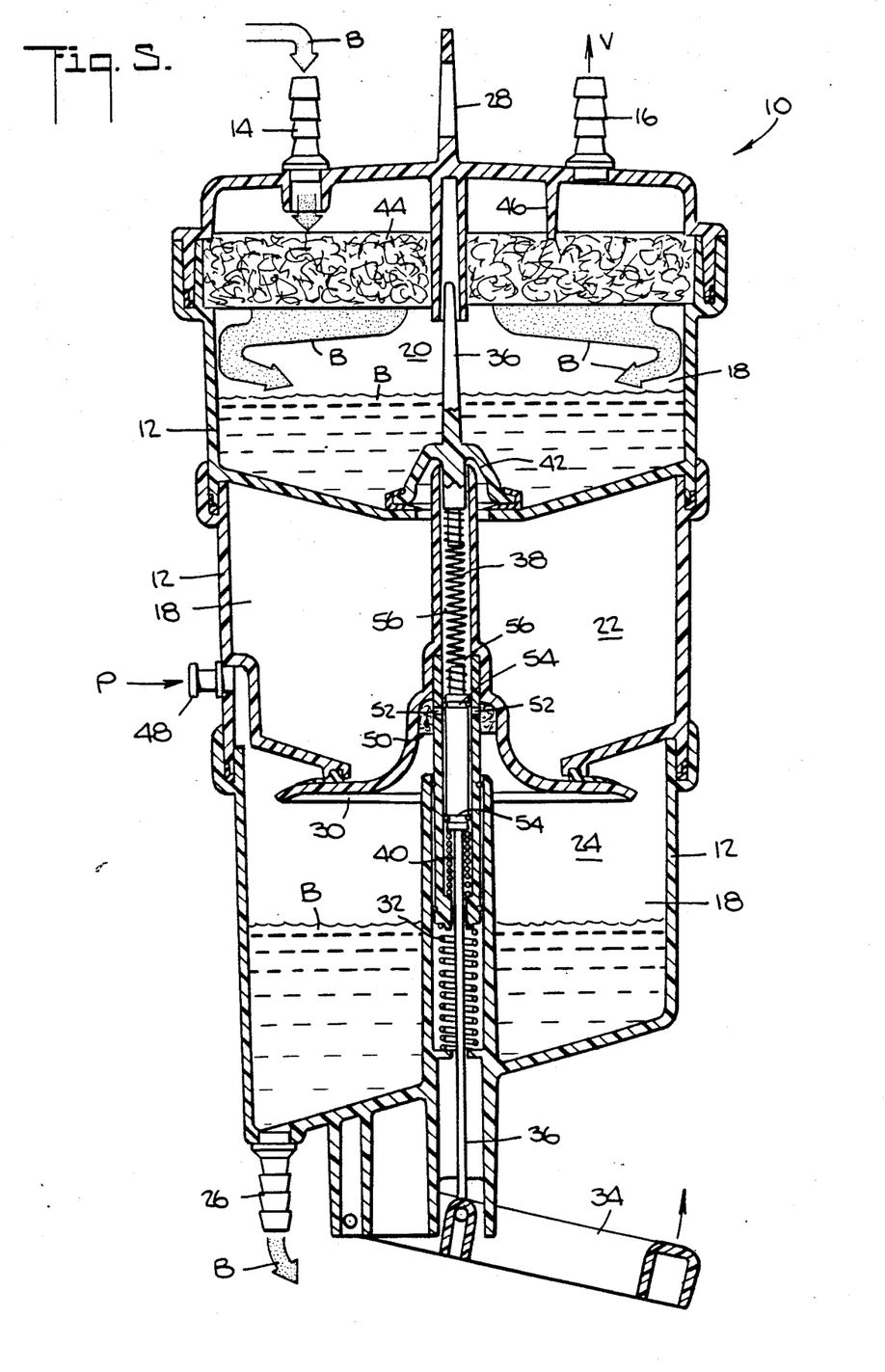
FIG. 5 is similar to FIG. 4 but showing an empty and segregated fluid isolation chamber.
Figure 6:
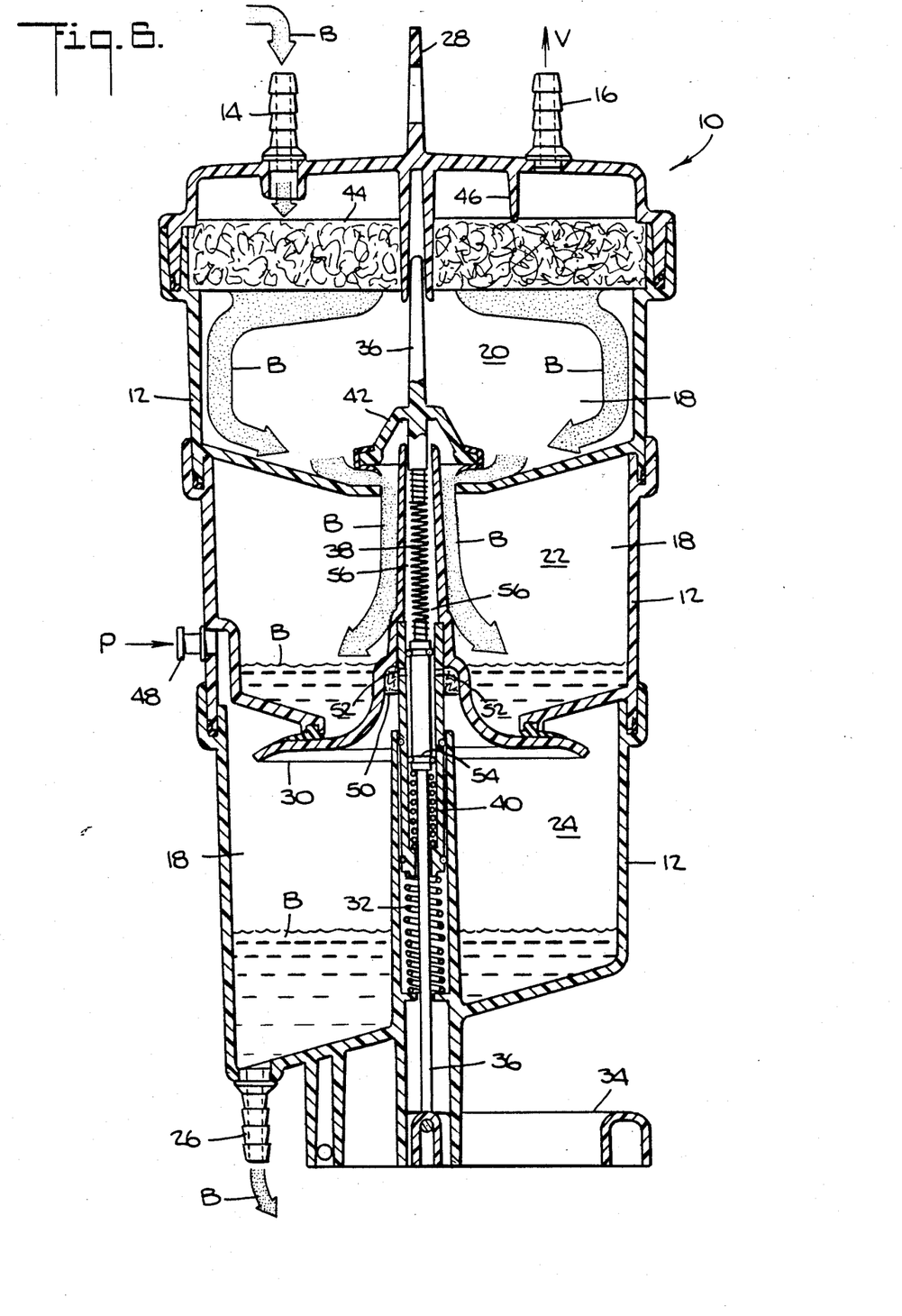
FIG. 6 is a view substantially as the fluid collecting operation depicted in FIG. 2 but while also depicting the simultaneous delivery of fluid out of the reservoir.
Figure 7:
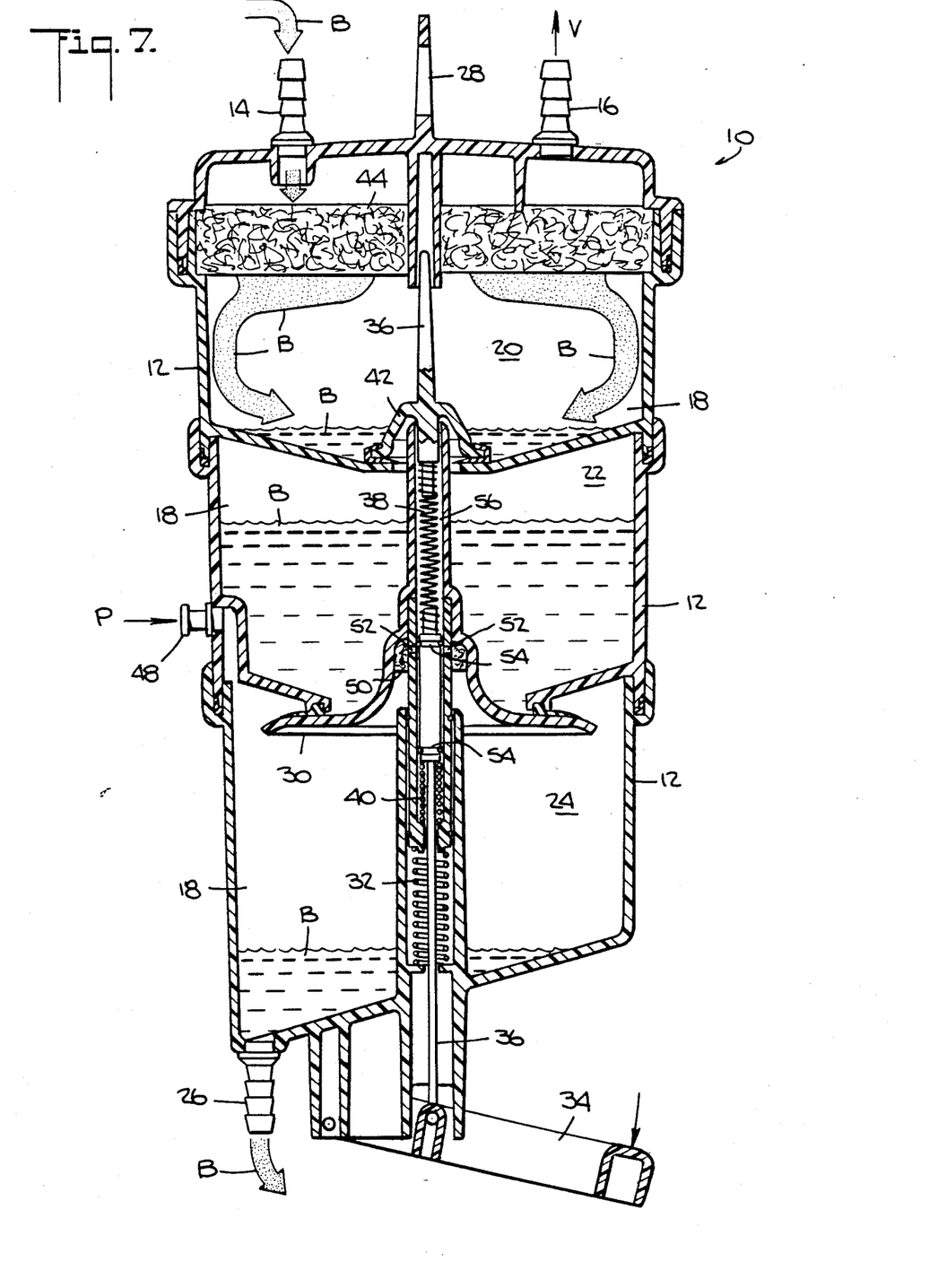
FIG. 7 is substantially the illustration provided in FIG. 3 but also showing the simultaneous delivery of fluid out of the reservoir.

FIG. 5 depicts the next sequence in the collection and delivery process wherein the direction of movement of lever 34 is reversed so that valve 30 is again seated to create a fluid seal between compartments 22 and 24. The energy stored in springs 32, 38 and 40 assist lever 34 in this return direction. It should be noted that valve 42 remains seated after the reseating of valve 30 and that blood continues to be simultaneously collected in compartment 20 while blood is delivered out of the reservoir through blood outlet port 26. FIG. 6 shows the next collection and delivery sequence wherein lever 34 is returned to its starting location. Member 36 has moved upwardly (assisted by energy stored in compressed spring 40) and valve 42 is unseated for allowing blood collected in compartment 20 to flow into compartment 22. Valve 30 remains seated and blood continues to be drawn into and delivered out of reservoir 10. FIG. 7 depicts the view substantially as that shown in FIG. 3 but additionally shows previously collected and transferred blood flowing out of compartment 24. The loop is now complete and the next step would be to repeat the FIG. 4 illustration.

Figure 8:
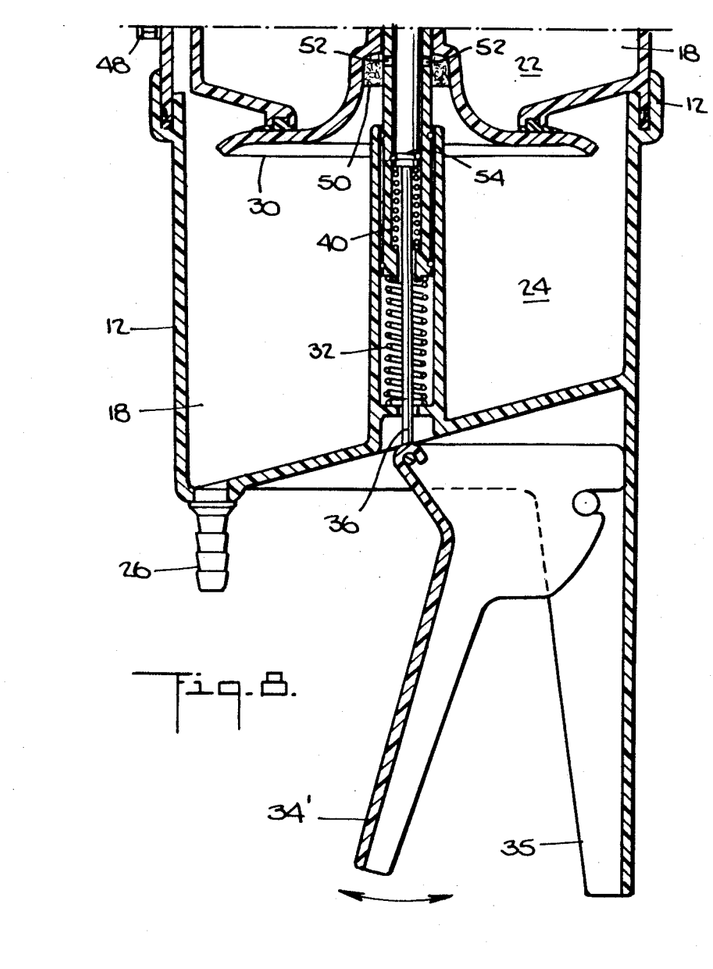
FIG. 8 is a view of the lower portion of the reservoir depicting an alternate configuration for reservoir activation.

Turning next to FIG. 8, there is shown an alternate embodiment of lever 34. Here there is depicted a lever 34', which forms a finger grip, and extension 35, which can be placed in the palm of a hand, so that the movement of member 36 and operation of internal reservoir structure as heretofore described can be accomplished by moving lever 34' in the directions indicated by the arrows. Counterclockwise movement of lever 34' performs the functions achieved through the downward movement of lever 34. Likewise, the return clockwise movement of lever 34' achieves the functional result of moving lever 34 upwardly.

Figure 9:
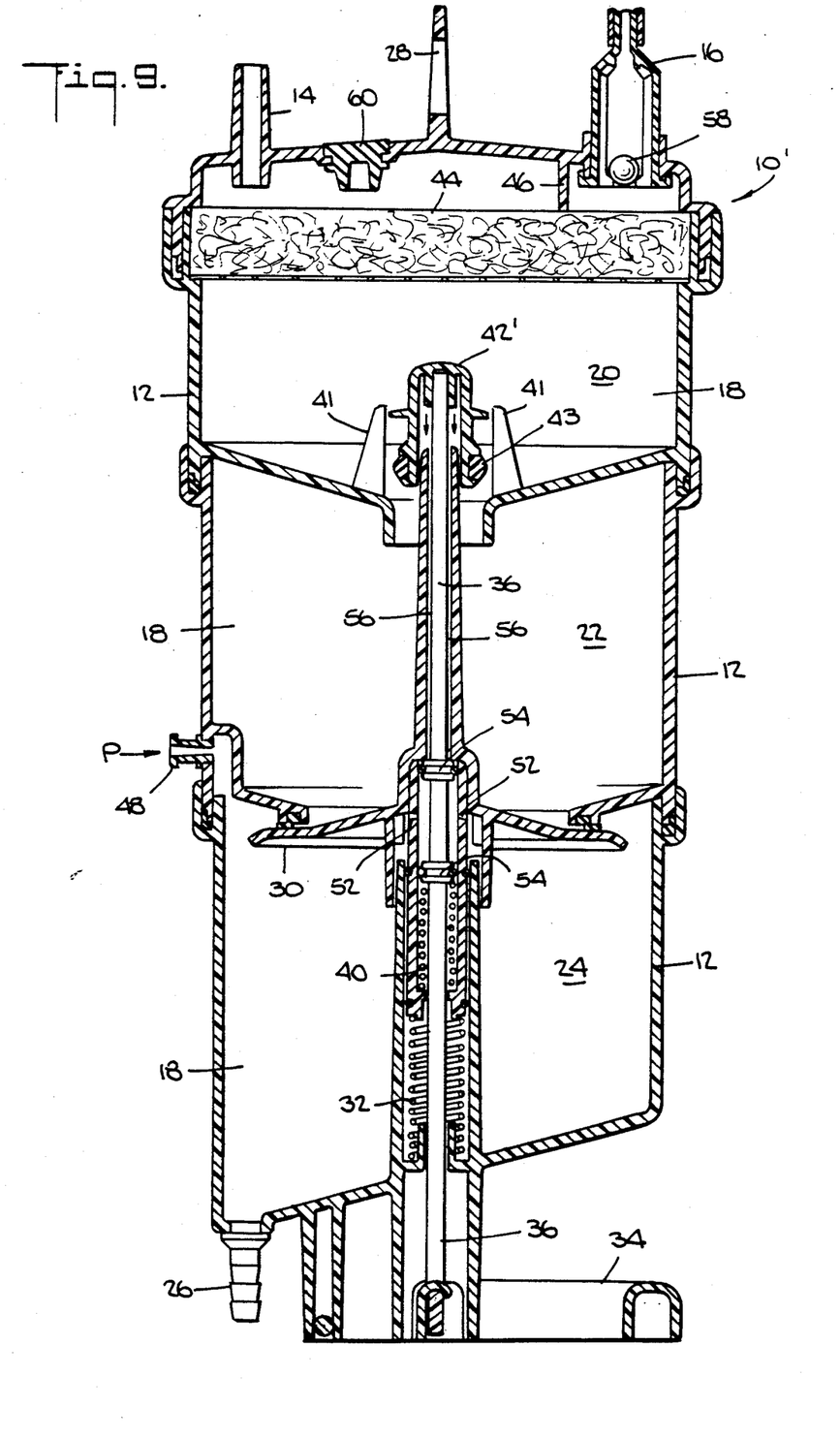
FIG. 9 is a view of another reservoir construction, the view being similar to FIG. 2 but without fluid collection, showing a modified internal reservoir activation mechanism.

Lastly, turning to FIG. 9, there is shown the structure of reservoir 10 much like that depicted in FIGS. 2-7. Here we have designated the reservoir 10' and the different structural features depicted are valve 42', valve guide ribs 41 and seal ring 43. Spring 38 has been eliminated and elongated member 36 is continuous from lever 34 to valve 42 which is secured to member 36. Movement of valve 42', upon activation of lever 34 as heretofore described, is shown by the arrows. Upon deflection of lever 34, valve 42' moves downwardly and seal ring 43 creates a fluid seal between compartments 20 and 22. The movement of parts, collection and transfer of blood and delivery of blood out of reservoir 10' are as described in respect to reservoir 10. Additional features depicted in this view are ball float valve 58 (designed to prevent blood flow out of vacuum port 16) and medication port 60 (included so that medicine may be added to the blood if desired.

A method of blood collection can be accomplished using either a patient or a reservoir as a blood source and collecting blood into and delivery out of the above-described inventive reservoir for conveyance of the collected blood to either the patient or a reservoir. Operation of the inventive reservoir would be as previously described.

It should be appreciated that the reservoir herein disclosed is so designed that preferably the blood flow path through the reservoir is as shown in the drawing figures. A blood flow path as shown, with blood cascading along the reservoir walls and central blood flow control mechanism, would present a smooth blood transport pathway to reduce the amount of turbulence and subsequent risk of hemolysis.

While in accordance with provisions of the statutes there are described herein specific embodiments of the invention, those skilled in the art will understand that changes may be made in the form of the invention covered by the claims appended hereto without departing from the scope and spirit thereof, and that certain features of the invention may sometimes be used to an advantage without corresponding use of the other features.

We claim:

1. A fluid collection reservoir comprising a housing having at least one inlet and at least one outlet, three or more fluid receiving compartments, with a first compartment being in fluid flow communication with said inlet and with a second compartment being in fluid flow communication with said outlet, means for establishing a negative pressure in two or more of said compartments, means for mechanically and selectively isolating said compartments, and means for maintaining said second compartment at a pressure always greater than the pressure established in said first compartment while collecting and transporting fluid through said reservoir.

2. The reservoir according to claim 1 wherein said compartments number three.

3. The reservoir according to claim 2 further including lever means for imparting movement to a mechanism for controlling blood transport through said reservoir, said mechanism comprising an elongated member at a first end engaging said lever, a resilient member urging a first valve into position for creating a first fluid seal between a second and a third of said compartments, said elongated member at a second end supporting a second valve, said elongated member being adapted for movement in a first direction for creating a second fluid seal between said second compartment and a first of said compartments and then to deflect said resilient member unseating said first valve and releasing said first fluid seal.

4. The reservoir according to claim 3 wherein said elongated member is further adapted for movement in a second direction, opposite said first direction, to first reposition said first valve reestablishing said first fluid seal and then to reposition said second valve for releasing said second fluid seal.

5. The reservoir according to claim 4 further including means for selectively establishing a positive pressure in said third compartment.

6. The reservoir according to claim 5 further including means for equalizing pressure between said second and said third compartments before releasing said first fluid seal.

7. The reservoir according to claim 6 wherein said means comprises vent means disposed in said third compartment adapted for opening to create a passageway between said second and said third compartments.

8. The reservoir according to claim 3 further including means for venting said third compartment to ambient.

9. The reservoir according to claim 1 further including filtration means for filtering entering fluid for gross particulate removal and foam reduction.

10. An autologous blood recovery system comprising
a housing including a collection chamber formed therein, with the collection chamber having a plurality of compartments;
an inlet in said housing adapted to be connected to a patient for conveying blood from said patient into a first compartment of said collection chamber;
means for providing fluid flow communication between said first compartment and a second of said compartments;
means for creating a first fluid seal between said second compartment and a third of said compartments;
means for establishing a negative pressure in said first and said second compartments, with said negative pressure being sufficient for maintaining a flow of blood into said collection chamber;
means for maintaining said third compartment at a pressure greater than the pressure established in said first and second compartments;
means for creating a second fluid seal between said first and second compartments while compartments said first fluid seal;
means for releasing said first fluid seal and providing fluid flow communication between said second and said third compartments; and
an outlet adapted to convey blood out of said collection chamber for reinfusion into said patient.

11. The system according to claim 10 further including means for venting said third compartment to atmosphere.

12. The system according to claim 10 further including means for reestablishing said first fluid seal, and means for releasing said second fluid seal and reestablishing fluid flow communication between said first and said second compartments while maintaining said reestablished first fluid seal.

13. The system according to claim 10 wherein said housing further includes filtration means for filtering entering blood for gross particulate removal and foam reduction.

14. The system according to claim 13 wherein said housing further includes baffle means disposed between said inlet and said negative pressure establishing means. with said baffle means substantially contacting said filtration means for diverting blood flow away from said negative pressure establishing means.

15. The system according to claim 10 further including means for equalizing pressure between said second and said third compartments before releasing said first fluid seal.

16. The system according to claim 15 wherein said means comprises vent means disposed in said third compartment adapted for opening to create a passageway between said second and said third compartments.

17. The system according to claim 10 further including lever means for imparting movement to a mechanism for controlling blood transport through said collection chamber, said mechanism comprising an elongated member at a first end engaging said lever. a resilient member urging a first valve into position for creating said first fluid seal, said elongated member at a second end supporting a second valve. said elongated member being adapted for movement in a first direction to first urge said second valve into position for creating said second fluid seal and then to compress said resilient member unseating said first valve and releasing said first fluid seal.

18. The system according to claim 17 wherein said elongated member is further adapted for movement in a second direction, opposite said first direction. to first reposition said first valve, reestablishing said first fluid seal, and then to reposition said second valve for releasing said second fluid seal.

19. The system according to claim 10 further including means for selectively establishing a positive pressure in said third compartment.

20. The system according to claim 19 wherein said means comprises a sphygmomanometer bulb. a pressure gauge, and tubing communicating with a port in said third compartment.

21. The system according to claim 19 wherein said pressure ranges from about atmospheric to about 200 millimeters of mercury.

22. The system according to claim 20 further including means for filtering pressuring air entering said third compartment.

23. The system according to claim 22 wherein said means comprises a bacterial filter having a pore size of less than about 1.0 u.

24. The system according to claim 23 wherein said pore size is equal to or less than about 0.45 u.

25. The system according to claim 11 wherein said means for establishing said negative pressure is a vacuum port in said housing adapted to be connected to a source of suction.

26. The system according to claim 25 wherein said vacuum port further includes means for preventing outflow of blood through said vacuum port.

27. A reservoir for collecting and delivering blood comprising
a housing defining a collection chamber having a plurality of compartments;
an inlet for introducing blood into a first compartment of said collection chamber;
means for providing fluid flow communication between said first compartment and a second of said compartments;

means for creating a first fluid seal between said second compartment and a third of said compartments;

means for establishing a negative pressure in said first and said second compartments;

means for maintaining said third compartment at a pressure greater than the pressure established in said first and second compartments;

means for creating a second fluid seal between said first and said second compartments while maintaining said first fluid seal;

means for releasing said first fluid seal and providing fluid flow communication between said second and said third compartments; and an outlet for conveying blood out of said collection chamber.

28. The reservoir according to claim 27 further including means for venting said third compartment to ambient.

29. The reservoir according to claim 27 further including means for reestablishing said first fluid seal, and means for releasing said second fluid seal and reestablishing fluid flow communication between said first and said second compartments while maintaining said reestablished first fluid seal.

30. The reservoir according to claim 27 wherein said housing further includes filtration means for filtering entering blood for gross particulate removal and foam reduction.

31. The reservoir according to claim 30 wherein said housing further includes baffle means disposed between said inlet and said negative pressure establishing means, with said baffle means substantially contacting said filtration means for diverting blood flow away from said negative pressure establishing means.

32. The reservoir according to claim 27 further including means for equalizing pressure between said second and said third compartments before releasing said first fluid seal.

33. The reservoir according to claim 32 wherein said means comprises vent means disposed in said third compartment adapted for opening to create a passageway between said second and said third compartments.

34. The reservoir according to claim 27 further including lever means for imparting movement to a mechanism for controlling blood transport through said collection chamber, said mechanism comprising an elongated member at a first end engaging said lever, a resilient member urging a first valve into position for creating said first fluid seal, said elongated member at a second end supporting a second valve, said elongated member being adapted for movement in a first direction to first urge said second valve into position for creating said second fluid seal and then to deflect said resilient member unseating said first valve and releasing said first fluid seal.

35. The reservoir according to claim 34 wherein said elongated member is further adapted for movement in a second direction, opposite said first direction, to first reposition said first valve, reestablishing said first fluid seal, and then to reposition said second valve for releasing said second fluid seal.

36. The reservoir according to claim 27 further including means for selectively establishing a positive pressure in said third compartment.

37. The reservoir according to claim 36 wherein said means comprises a sphygmomanometer bulb, a pressure gauge, and tubing communicating with a port in said third compartment.

38. The reservoir according to claim 36 wherein said pressure ranges from about atmospheric to about 200 millimeters of mercury.

39. The reservoir according to claim 37 further including means for filtering pressurizing air entering said third compartment.

40. The reservoir according to claim 39 wherein said means comprises a bacterial filter having a pore size of less than about 1.0 u.

41. The reservoir according to claim 40 wherein said pore size is equal to or less than about 0.45 u.

42. The reservoir according to claim 27 wherein said means for establishing said negative pressure is a vacuum port in said housing adapted to be connected to a source of suction.

43. The reservoir according to claim 42 wherein said vacuum port further includes means for preventing outflow of blood through said vacuum port.

* * * * *